United States Patent [19]

Frankel et al.

[11] Patent Number: 4,679,571
[45] Date of Patent: Jul. 14, 1987

[54] BLOOD SAMPLE NEEDLE ASSEMBLY WITH VEIN INDICATOR

[75] Inventors: Eric Frankel, New York, N.Y.; Andrzej J. Plucinski, Norwood, N.J.

[73] Assignee: Becton, Dickinson and Company, Franklin Lakes, N.J.

[21] Appl. No.: 645,893

[22] Filed: Aug. 31, 1984

[51] Int. Cl.$^4$ ............................................. A61B 5/14
[52] U.S. Cl. .................................. 128/764; 128/765; 604/190
[58] Field of Search ..................... 128/760, 762–767; 604/125, 126, 187, 190, 263

[56] References Cited

U.S. PATENT DOCUMENTS

| | | | |
|---|---|---|---|
| 3,401,692 | 9/1968 | Harris, Jr. | 604/125 |
| 3,661,815 | 5/1972 | Smith | 252/54.32 |
| 3,935,099 | 1/1976 | Weaver et al. | 210/689 |
| 3,960,139 | 6/1976 | Bailey | 128/762 |
| 3,985,616 | 10/1976 | Weaver et al. | 435/178 |
| 3,997,484 | 12/1976 | Weaver et al. | 525/54.31 X |
| 4,045,387 | 8/1977 | Fanta et al. | 128/156 X |
| 4,134,863 | 1/1979 | Fanta et al. | 604/368 |
| 4,159,260 | 6/1979 | Jones et al. | 525/492 X |
| 4,190,426 | 2/1980 | Ruschke | 604/126 X |
| 4,207,870 | 6/1980 | Eldridge | 128/766 |
| 4,340,067 | 7/1982 | Rattenborg | 128/763 |
| 4,385,637 | 5/1983 | Akhavi | 128/763 |
| 4,398,544 | 8/1983 | Nugent et al. | 128/763 |
| 4,416,290 | 11/1983 | Lutkowski | 128/764 |
| 4,416,291 | 11/1983 | Kaufman | 128/764 X |
| 4,418,703 | 12/1983 | Hoch et al. | 128/766 |
| 4,436,098 | 3/1984 | Kaveman | 128/766 |
| 4,519,402 | 5/1985 | Andersen | 128/766 X |

OTHER PUBLICATIONS

Water-Lock Product Data Sheet; Grain Processing Corp.

Primary Examiner—Kyle L. Howell
Assistant Examiner—Angela D. Sykes
Attorney, Agent, or Firm—R. P. Grindle

[57] ABSTRACT

A liquid sample needle assembly is provided. The assembly includes a housing with a sample receiving chamber having translucent or transparent walls for determining whether access to the sample source in question has been obtained. The invention utilizes a highly absorbent material in a form which allows venting of gases displaced from the housing chamber by the liquid sample being obtained, which material expands upon contact with the liquid sample to provide a liquid impervious barrier. The absorbent material is in a separate sleeve-like form of a compacted tablet sleeve for rapid and easy insertion between the two hub parts forming the assembly housing. The improvement in this invention includes the use of an integral tapered post for seating the tablet to maintain it precisely concentric in the housing and on the post for causing each increment of the tablet to respond equally to an introduced sample. The arrangement herein is particularly appropriate for mass production techniques in that two housing parts may have inserted therein the separately formed tablet sleeve.

13 Claims, 6 Drawing Figures

BLOOD SAMPLE NEEDLE ASSEMBLY WITH VEIN INDICATOR

BACKGROUND AND STATEMENT OF THE INVENTION

This invention relates to the invention described and claimed in co-pending application Ser. No. 562,309 filed Dec. 16, 1983, and which is hereby incorporated by reference in its entirety.

The invention herein is incorporated into an assembly for collecting a liquid sample from a patient, such as a blood sample. More particularly, this invention relates to a needle assembly for collecting single and multiple liquid samples from such a patient with the use of the single assembly herein. The device utilizes a housing chamber for the samples with walls which are translucent or transparent, for visually indicating whether or not proper access to the sample source in question has been achieved.

Moreover, a material which is highly absorbent to aqueous containing solutions is utilized in the form of a substantially cylindrical sleeve providing air passage so that gas displaced by a liquid sample moving into the housing chamber may be vented, followed by an immediate swelling of the material upon exposure of the liquid sample to prevent any discharge of the liquid sample from the housing chamber. The sleeve is comprised of a solid compacted material which is of a size allowing an air bleed passage between the walls of the sleeve and the adjacent walls of the housing containing the sleeve. The material swells on contact with the liquid closing the bleed passage or passages.

As taught in the above-referenced co-pending application, the tablet forming the cylindrical sleeve seals the chamber against discharge of the sample, while simultaneously providing for the venting of gas displaced by that same sample. Once entry has been made to the source of the liquid sample, as indicated by the transparent or translucent chamber walls visually showing the presence of the sample in the housing chamber, then multiple samples may be collected from the housing chamber by being drawn sequentially into a plurality of vacuum collection devices. The assembly incorporates a separate flexible self-sealing elastomeric sleeve which cooperates with the discharge opening of the device during periods of exchange of the vacuum collection devices for sequential discharge of additional samples.

In certain instances, it has been found that when the compacted tablet sleeve embodiment described in co-pending application Ser. No. 562,309 is used, due to radial clearances present in the assembly, it is possible for the tablet to move to one side, presenting a much larger opening to flow than if clearances were concentric. This may be caused simply by gravity. At any rate, this causes a momentary uneven response to the initial quantity of blood, and has the effect of a slight delay in blocking blood flow during the initial vein entry indication procedures for taking a blood sample.

With this invention by contrast, the tablet cylinder or sleeve is mounted on a tapered hub post. The taper is such that the hub post diameter increases toward the negative pressure end of the device. This causes a wedging action which holds the tablet sleeve axis concentric to the cooperating hub axis to form a device which reacts evenly around its entire circumference to the sample. Because of this, there is an even response in the form of initial venting of air pockets in the assembly when vein entry has been achieved through the sleeve, followed rapidly and almost simultaneously by a swelling of the compacted sleeve material to block blood flow before an evacuated sample receiving tube is attached to the negative cannula end of the assembly. Thus, at the moment when the blood comes into contact with the sleeve, the sleeve expands evenly and concentrically around its supporting hub by absorbing the aqueous content of the blood sample, and preventing any further movement past the sleeve.

As discussed above, it is desirable to provide a mechanism whereby the user of such a needle assembly can be informed when the intravenous needle has penetrated the source of the sample to be obtained, such as the vein of the patient for collection of a blood sample. Many times in collecting blood from a patient, it is difficult to locate the vein, or for other reasons blood flow into the collecting device is not adequate. In those instances, it is advantageous to be able to make a quick determination that entry into the vein has been made, and that blood is flowing into the needle assembly. Once this determination has been made and the vein entry achieved, the evacuated blood collection containers can be inserted into the collection assembly in accordance with well known techniques of collecting blood samples during a collection procedure involving a single vein entry.

The invention here is arranged to overcome one of the problems which arises during the venipuncture step in that pockets of air are present in the various needle assemblies. When veni-puncture is made, and the evacuated blood collection container is not yet attached to the opposite end of the structure, blood cannot flow into the needle assembly because of a pocket of air which, under normal atmospheric conditions, remains inside the needle assembly. Thus, even though vein entry may have been accomplished, blood flow may not begin, simply because of the air pocket blockage in the assembly.

Both U.S. Pat. Nos. 4,207,870 and 4,398,544, assign to the common assignee herewith, utilize a porous plug in blood collection assemblies of the kind described herein. Both of these arrangements utilize a material which is air pervious and liquid impervious. The material is a sintered material which is occluded by the movement of a blood sample into the interstices of the porous material. Both patents describe inventions utilizing relatively complicated valve structures, including movable internal parts. Although the inventions recognize the utilization of a porous material for providing a venting for displaced air during receiving a blood sample, there is still room for improvement over such a device. That is, absolute positive sealing may not always be achieved merely by physical occlusion, although generally such procedures are effective.

By contrast, in the present invention, the material is in the form of a separate sleeve or tablet which may be inserted in a mechanical manner between the two parts forming a housing during the construction thereof in a production line. The arrangement herein is a simplified structure comprising a highly absorbent material in the form of a cylinder, which swells in contact with aqueous substances. The material is of the highly absorbent material compressed from that material into a sleevelike cylindrical tablet form, which is inserted mechanically between the two parts forming the housing. As will be understood by practitioners-in-the-art of constructing multiple blood collection assemblies, these cylinders may be formed separately in large numbers for insertion in a mass production line between the two parts forming the housing, with all such procedures being handled by robots.

Before describing this invention in more detail, it may be well to note that the material forming the substantially cylindrical vent sleeve of the invention may be comprised of a hydrolyzed starch-polyacrylonitrile graft copolymer with side chains containing carboxamide and carboxylate groups, such as WATER-LOCK A100, WATER-LOCK A125, ducts of Grain Processing Corporation, 1600 Oregon Street, Muscatine, Iowa 52761. Other sources include Henkel Corporation, 4620 West 77th Street, Minneapolis, Minn., Super Absorbent Company, Route 3, P.O. Box 342, Lumberton, N.C. and Edison Hydrocontrol Chemicals Inc., 99 Madison Avenue, New York, N.Y. 10016.

The absorbent polymeric compositions of the invention may be prepared by the procedures taught in U.S. Pat. Nos. 4,045,387; 4,134,863; 3,981,100; 4,159,260; 3,661,815; 3,935,099 and 3,985,616.

Other objects and advantages of this invention will be apparent from the following description, the accompanying drawings and the appended claims.

DETAILED DESCRIPTION OF THE DRAWINGS

Figure 1:
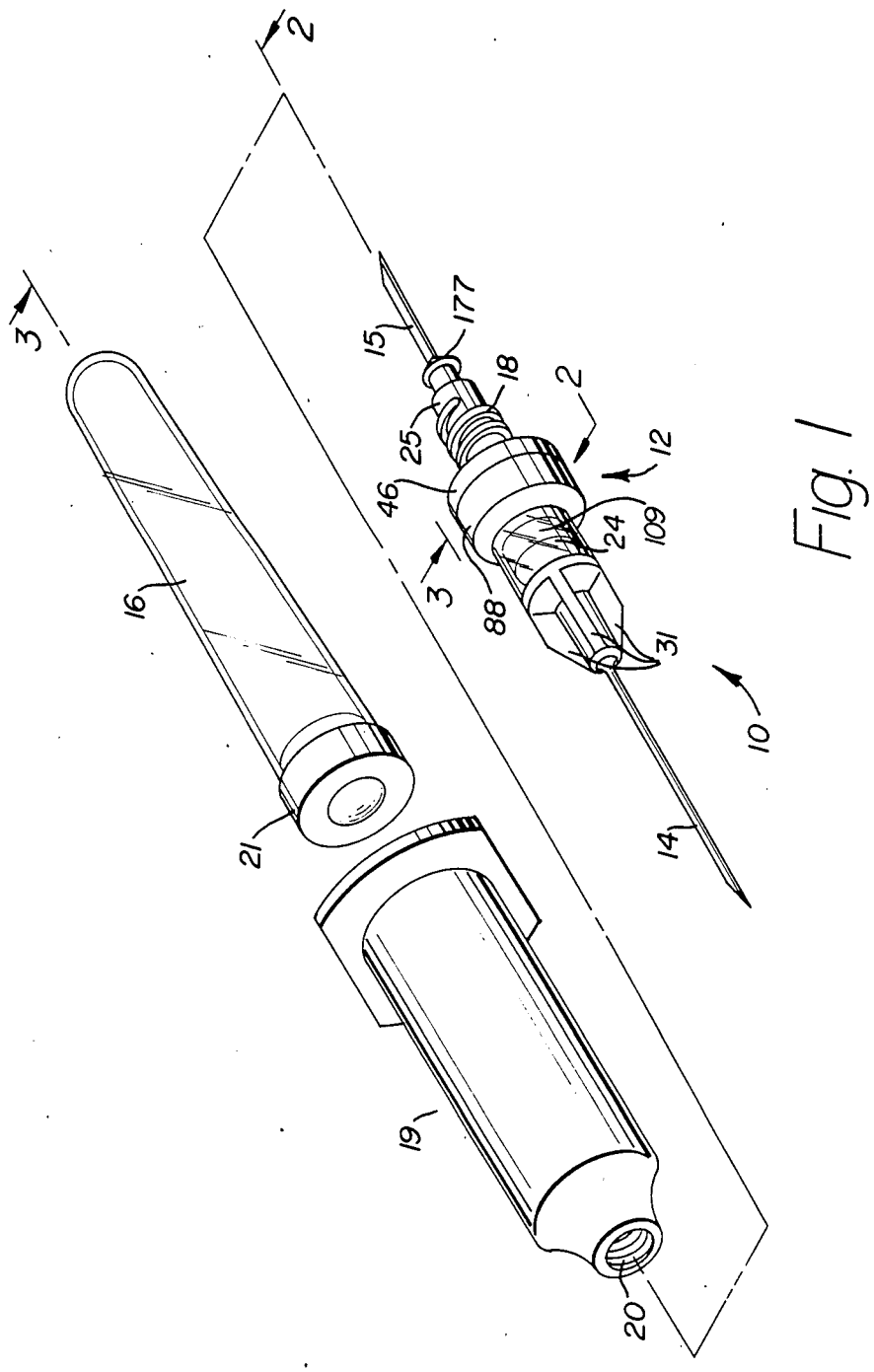
FIG. 1 is an exploded perspective view illustrating generally the standard parts and arrangements of a sample collection needle assembly, including a holder for an evacuated container and an evacuated blood collection container for use in obtaining blood samples from a patient.
Figure 5:
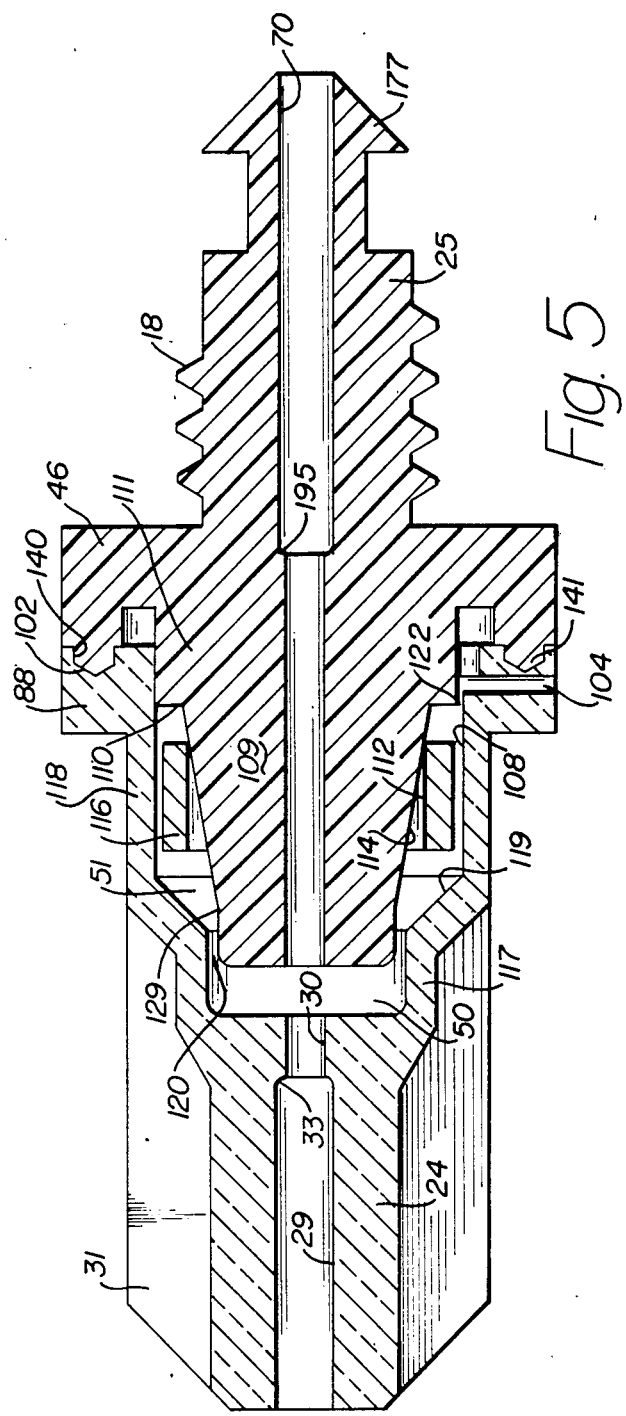
Figure 6:
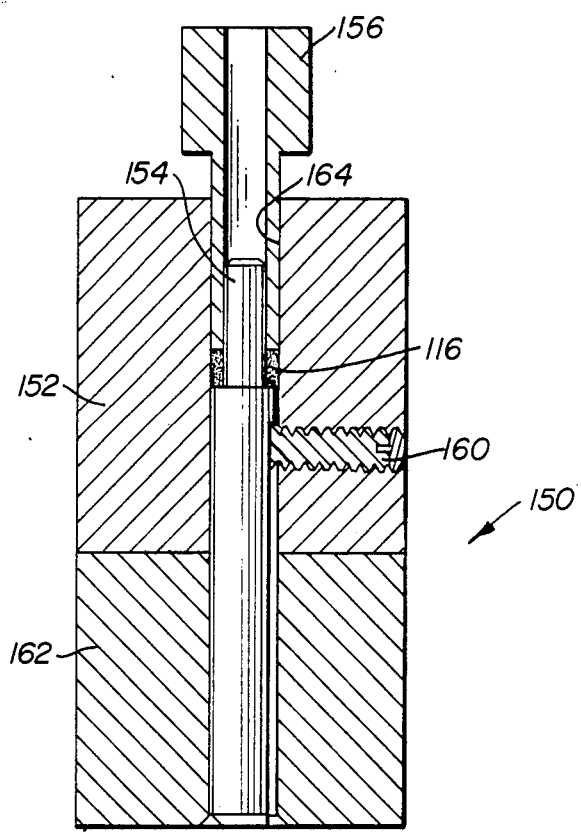

FIG. 5 is an enlarged sectional view of the housing assembly of FIG. 1 with the cannulas removed, and showing the two-part assembly of the housing in the form of a intravenous hub and a negative pressure hub having formed therebetween one embodiment of the sleeve and tapered supporting hub post of the invention; and FIG. 6 is a sectional view in elevation showing a device for forming the compacted cylindrical sleeve or tablet, forming part of the invention herein.

DETAILED DESCRIPTION OF THE INVENTION

Referring to the drawings in which like reference characters refer to like parts throughout the several views thereof, FIG. 1 shows the basic external components of needle assembly 10, including a housing 12, a first intravenous (I.V.) needle cannula 14 adapted for insertion into a patient and a second negative pressure needle cannula 15 at the opposite end of housing 12. The second needle cannula 15 is adapted for penetration into an evacuated container 16 for collection of a blood sample. It will be understood by practitioners in the art that a single needle structure, extending through the assembly, may be used as a substitute for the dual needle assembly 14, 15 described herein. The dual assembly described is merely illustrative of the environment of the invention here. Housing 12 includes a negative pressure hub portion 25 having threads 18 adjacent the second cannula 15 onto which a container holder 19 is threaded by its internal mating threads 20 at the forward end of the holder. Evacuated container 16 is inserted into holder 19 so that second needle cannula 15 penetrates the stopper 21 at the forward end of the evacuated container 16. These general aspects of blood sample collection assemblies are well known to those skilled in the art.

Figure 2:
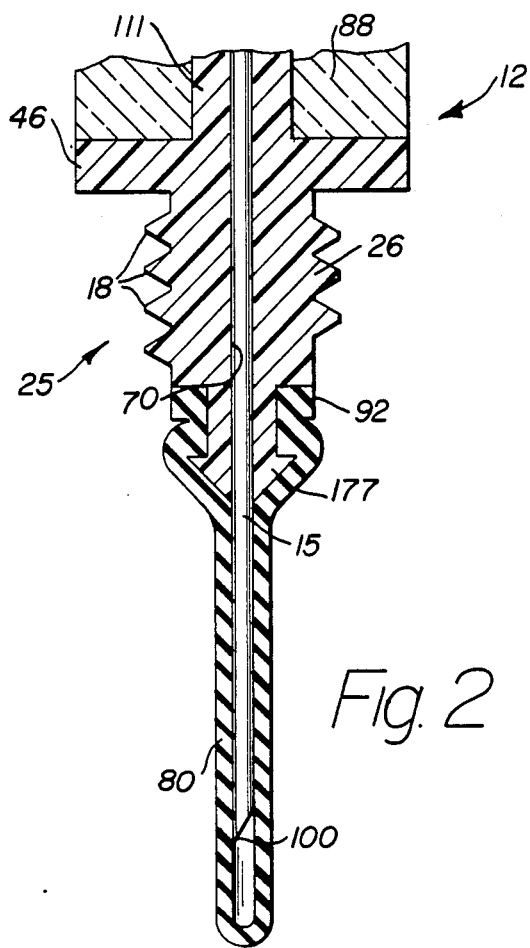
FIG. 2 is a partial enlarged cross-sectional view taken along lines 2—2 of FIG. 1 and illustrating the separate elastometric sleeve valve utilized in the assembly herein.

Referring now to FIG. 2, negative pressure hub end 25 of housing 12 is shown, and includes a cylindrical portion 111 for cooperation with a bore in the forward intravenous hub 24 to be described below. A flange 46 is arranged to cooperate with a flange 88 on forward I.V. hub 24, again as to be described below. A bore 70 extends through the rearward end 25 of the housing. Bore 70 is sized to accept the diameter of second needle cannula 15, extending to seat 195 (FIG. 5) which is secured to bore 70 by appropriate means such as adhesives, for example. It is within the purview of the invention, as will be described in more detail below that the two hubs may be joined together by sonic welds or other appropriate joining procedures well known in the art.

Figure 3:
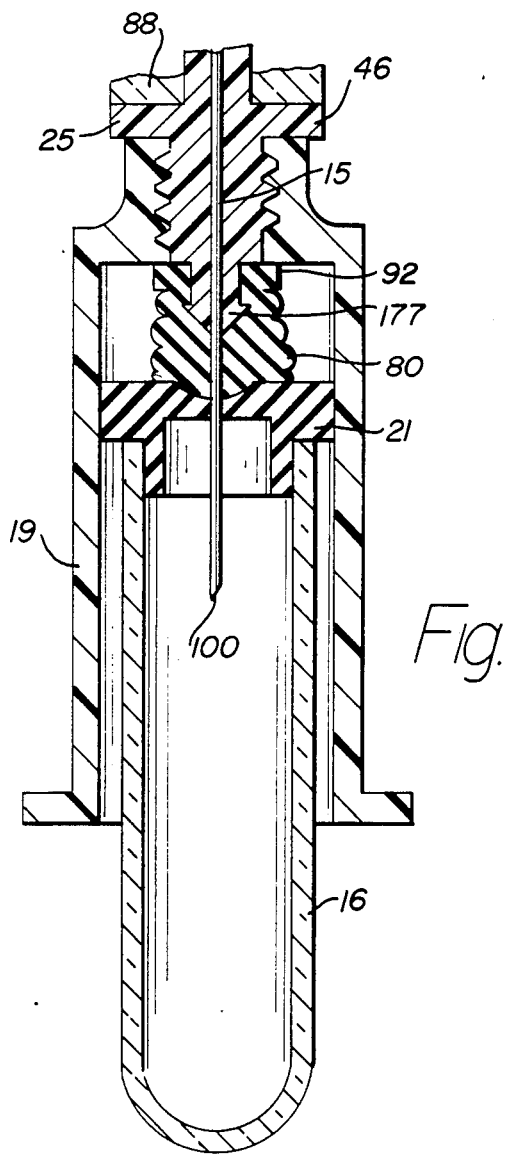
FIG. 3 is a partial enlarged cross-sectional view taken along lines 3—3 of FIG. 1.
Figure 4:
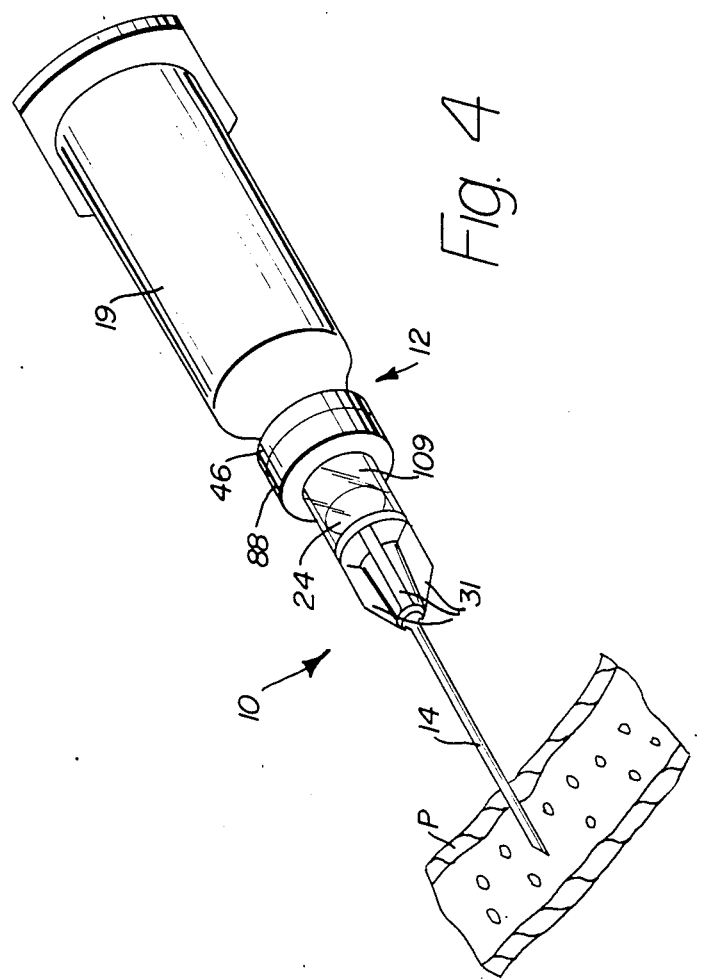
FIG. 4 is a perspective view of a needle assembly connected to a holder inserted into a patient so that a user can view the assembly for indication of vein entry.

As can be seen in FIG. 2, negative pressure cannula 15 ends in a point 100 which is arranged to penetrate the stopper 21 of an evacuated container 16. Covering the negative pressure end of cannula 15 is a self-sealing elastomeric sleeve 80 having a flange 92 thereon. Thus, when point 100 is forced into and through the central penetrable diaphragm of stopper 21, point 100 first penetrates the end of flexible sleeve 80 and forces sleeve 80 to collapse, as shown in FIG. 3. In this connection, the internal surface of flange 92 adjacent cannula 15 includes provisions (not shown) for engaging annular snap-on barb 177 on extension 26. This provides for a snap-fit engagement of sleeve 80 over cannula 15. It will be understood that other forms of connection may be used.

Referring now to FIG. 5, I.V. hub 24 includes a bore 29 therein for receiving I.V. cannula 14. Hub 24 includes a rear extention 117 of larger diameter, which defines a housing chamber 50 therein for receiving a blood sample. Integrally formed at the rear of extension 117 is a further cylindrical portion 118 having a larger internal bore 108 forming an offset 119 at the juncture of chamber 50 and bore 108.

Forming a communication between bore 29 and chamber 50 is a bore 30 of smaller diameter than bore 29. The offset 33 between bores 29 and 30 serves as a seat for the internal end of I.V. cannula 14. Surrounding the forward portion of hub 24 are a plurality of ribs 31 which cooperate with internal ribs on a shield, not shown, conventionally utilized to cover the intravenous cannula 14, until such time as it is to be used.

Negative pressure hub 25, forward of the flange 46, includes an integral cylindrical forward extension 111, followed by a further forward integral cylindrical extension or hub post 109. Extension 109 is of lesser diameter than portion 111 to define an offset 110 therebetween. Hub post 109 cooperates with rear extensions 117, 118 of intravenous hub 24 to define an annular bleed passage 120, and an annular chamber 51. Annular chamber 51 defines the area for receiving the compressed sleeve or tablet 116 on the hub post 109 of the invention to be described below. Chamber 51 also serves as a vein entry indication chamber since the walls of 117, 118 are transparent or translucent. As discussed above, sleeve 116 may be comprised of compressed WATER-LOCK A125, a product of Grain Processing Corporation. As can be seen in FIG. 5, sleeve 116 may be formed and mounted on the hub post 109 of the negative pressure hub 25 prior to its insertion into the rear extension 117, 118 of I.V. hub 24.

In accordance with the invention here, hub post 109 is in the form of a supporting hub post for cylindrical compressed tablet or sleeve 116. Moreover, hub post 109 has a tapered surface 114 so that hub post 109 gradually increases in diameter in the negative pressure direction from point 129 to offset 110. This provides a wedging action between tablet sleeve 116 and surface 114 for holding tablet sleeve 116 concentric relative to the walls of chamber 51 and the surface 114. Thus, there is an equal response by tablet sleeve 116 in each annular increment thereof to bleed any air pockets from the device, and to swell immediately upon contact with the aqueous content of a sample.

Referring further to FIG. 5, it can be seen that midextension 111 of negative pressure hub 25 has a diameter slightly smaller than the diameter of bore 108 in order to define a vent passage at 122 which communicates with a vent 104 arranged in flange 88 forming the extreme rear end of I.V. hub 24. Flanges 46, 88 may be joined together to hold the entire assembly together by a sonic weld at 102. Alternatively, it will be appreciated by practitioners-in-the-art, that cooperating groove 140 and extension 141 formed in cooperating flanges 46, 88 may be joined together by an adhesive material, for example.

As purely illustrative of dimensions herein, passage 120 between chamber 50 and chamber 51 may have a radial extent of 0.0015 inches. That is, the front end of hub post 109 may have a diameter of 0.110 inches while the diameter of chamber 50 defined by annular extension 117 on I.V. hub 24 may be 0.113 inches. Bleed passage 122 may have a radial extent of 0.0015 inches, and preferably 0.0005 inches. That is, the diameter of extension 111 may be 0.217 inches while the diameter of bore 108 may be 0.220 inches.

As purely illustrative of further dimensions, the length of hub post 109 may be 0.28 inches, while the length of tapered surface 114 may be 0.155 inches. The angle of surface 114 from the axis of extension 109 is 1.2 degrees. That is, it is a Brown and Sharp Taper 0.500 inches on diameter per foot of length. With respect to compressed tablet or sleeve 116, the length may be within the range of between about 0.110 and 0.149 inches.

The internal diameter of the central opening or bore 112 of sleeve 116 is not particularly significant to the invention here as long as it is appropriate for securing the desired wedging and/or seating on extension 109. The bore 112 may be, for example, within the range of between about 0.111 and 0.114 inches. A significant dimension is the clearance between the outer surface of sleeve 116 and the walls of chamber 51. Generally, the diametral clearance will be within the range of between about 0.0001 inches and 0.004 inches clearance, and preferably 0.0005 inches clearance and 0.004 inches clearance. It is preferred that there be some clearance to start with in order to accommodate venting and, to a degree, within the very small dimensions involved, the swelling response of sleeve or tablet 116 to contact with an aqueous substance. Tablet or sleeve 116 is comprised of a compacted powder, compacted in a die to a density within the range of between about 0.80 and 1.1 grams per cubic centimeter (g/cc). The powder is designated WATER-LOCK ™ A125 a product of Grain Processing Corporation, manufactured under one or both of U.S. Pat. Nos. 3,661,815 or 4,159,260. The material is a starch-graft copolymer of polyacrylic acid and polyacrylamide. It has a density prior to compacting into the tablet sleeve of the invention of 0.34 grams per cubic centimeter. The WATER-LOCK A125 is representative only of one product which may be used in forming the sleeve 116.

Referring now to FIG. 6, a representative device 150 is shown for forming the tablet or sleeve 116 of the invention. It should be understood that this is for illustration only and that other devices may be used for compacting representative powders to the desired density. Thus, a die 152 is shown positioned on spacer 162, through the aid of locater pin 154. Pin 154 is retained in die 152 by means of set screw 160. The pin 154 is positioned centrally in bore 164 for forming the tablet or sleeve 116 of the invention in cooperation with a tamper 156. It will be understood, that the density of the tablet 116 formed by such a device will vary by changing the length of stroke and/or size of the charge used.

Thus, as will be appreciated from the above discussion, a blood collection needle assembly is provided in accordance with this invention for collecting single and multiple samples of blood from a single vein entry, as required, in combination with an arrangement for indicating vein entry to the user of the assembly. In this connection, it will be appreciated that the tablet or sleeve type arrangement serves to "flash" the presence of blood in the chamber of the assembly since the presence of blood in the sleeve will be shown through the transparent or translucent housing walls. The material, depending upon its dimension, its compression and/or density will immediately absorb the water content of the blood and will swell to the point of sealing off the chamber in the housing from any leakage of blood. This is almost immediately after a venting of any residual air in the housing chamber in order to allow the flow of intravenous blood from a source into the housing chamber.

With the tapered hub post upon which the compressed tablet is seated, the tablet is held in precise alignment with and concentric to the wall of the chamber and the hub post containing it so that each increment of the powder forming the tablet reacts simultaneously with the aqueous component introduced into the chamber for rapid swelling and closing of the air vent passage against any leakage of the sample, once the air venting has taken place.

Thus, there is almost an instantaneous, simultaneous bleeding of displaced air from the chamber and a sealing off of that chamber and a flashing or indication to the user that proper entry has been made to a patient's vein for obtaining the multiple samples. Subsequent to this indication, the user may then insert, sequentially, a plurality of evacuated tubes 16 onto the negative pressure cannula 15 with the sleeve valve 80 providing a self-sealing arrangement between the sequential removal and insertion of additional evacuated tubes 16 for taking the multiple samples of blood from the single source in a single entry into the vein.

The arrangement herein, is, of course, a throw-away device. Once the single or multiple samples have been taken from the single source, it is discarded. It is important, in this connection, to understand that the arrangement herein is a very inexpensive simplified arrangement wherein the separate sleeve may be mounted between the two parts forming the housing in accordance herewith as a separate piece of the assembly in a mass production line for producing literally thousands of an assembly in accordance with this invention in a rapid efficient highly mechanized manner. Nevertheless, the devices, though they are inexpensive throw-away type devices, function correctly and precisely for indicating vein entry, bleeding off displaced air, and providing appropriate positive sealing off of the chamber of the housing, once vein entry has been indicated by the device.

While the methods and forms of apparatus herein described constitute preferred embodiment of the invention, it is to be understood that the invention is not limited to these precise methods and forms of apparatus, and that changes may be made therein without departing from the scope of the invention which is defined in the appended claims.

What is claimed is:

1. A needle assembly for collecting one or more liquid samples from a source for subsequent discharge into evacuated containers, comprising
    (a) a housing having a forward end and a rearward end;
    (b) a sample collection chamber in said housing;
    (c) a first access opening in said forward end in liquid flow communication with said chamber;
    (d) a first cannula extending outwardly from said first access opening for insertion into said source;
    (e) a second access opening in said rearward end in flow communication with said chamber;
    (f) a second cannula positioned in said second access opening and in flow communication with said chamber;
    (g) valve means on said second cannula for controlling discharge of liquid samples from said chamber into evacuated containers attached to said second cannula;
the improvement characterized by
    (h) cooperating means on said forward end and said rearward end of said housing providing an annular fluid bleed passage means therebetween;
    (i) said fluid bleed passage means being separate from said second access opening and said second cannula;
    (j) vent means in said housing providing flow communication with said fluid bleed passage and ambient;
    (k) said cooperating means including a tapered hub post on said rearward end, said hub post extending into said chamber;
    (l) said hub post having a gradually increasing cross section from said forward end to said rearward end;
    (m) an annular compressed tablet forming a central bore positioned on said hub post and comprised of a material responsive to aqueous containing materials adapted to be introduced into said chamber for swelling and closing said fluid bleed passage upon contact with an aqueous containing material passing therethrough; and
    (n) whereby when said first cannula engages said source, aqueous containing liquid enters said chamber, forcing any gas therein through said fluid bleed passage and said vent means, and causing said liquid to come into contact with said tablet which swells and closes said fluid bleed passage.

2. The apparatus of claim 1, further characterized by said cooperating means including
    (a) an integral cylindrical extension on said rearward end of said housing;
    (b) an integral annular extension on said forward end of said housing;
    (c) an internal surface on said forward end extension;
    (d) an external surface on said rearward end extension; and
    (e) the said internal surface of said forward end extension cooperating with the said external surface of said rearward end extension to form an annular fluid bleed passage means therebetween.

3. The apparatus of claim 1, further characterized by said tablet comprising
    (a) an annular compressed tablet of hydrolyzed starch-polyacrylonitrile graft copolymer with side chains containing carboxamide and carboxylate groups.

4. The apparatus of claim 3, further characterized by
    (a) said annular tablet is comprised of powder compressed to a density of within the range of between about 0.80 and 1.1 grams per cubic centimeter.

5. The apparatus of claim 1, further characterized by
    (a) the clearance fit between said compressed tablet and the walls of said chamber containing said tablet is within the range of between about 0.0001 inches and 0.004 inches clearance.

6. The apparatus of claim 5, further characterized by
    (a) said clearance fit is within the range of between about 0.0005 inches clearance and 0.004 inches clearance.

7. The apparatus of claim 1, further characterized by
    (a) said housing including means for connecting a holder for an evacuated container.

8. The apparatus of claim 1, further characterized by
    (a) a holder for an evacuated container connected to said housing.

9. The apparatus of claim 1, further characterized by
    (a) said housing including means for viewing the contents of said chamber.

10. The apparatus of claim 9, further characterized by
    (a) said viewing means is transparent or translucent housing walls adjacent said chamber.

11. The apparatus of claim 1, further characterized by
    (a) said tapered hub post having a tapered surface; and
    (b) said tapered surface being at an angle of 1.2 degrees from the axis of said hub.

12. The apparatus of claim 11, further characterized by
    (a) said tapered surface being 0.155 inches long.

13. The apparatus of claim 1, further characterized by
    (a) the said central bore in said annular compressed tablet being within the range of between about 0.111 and 0.114 inches in diameter.

* * * * *